US006342355B1

(12) United States Patent
Hacia et al.

(10) Patent No.: US 6,342,355 B1
(45) Date of Patent: *Jan. 29, 2002

(54) PROBE-BASED ANALYSIS OF HETEROZYGOUS MUTATIONS USING TWO-COLOR LABELLING

(75) Inventors: Joseph G. Hacia, Rockville, MD (US); Mark S. Chee, Palo Alto, CA (US); Francis S. Collins, Rockville, MD (US)

(73) Assignees: The United States of America as represented by the Department of Health & Human Services, Washington, DC (US); Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/477,871

(22) Filed: Jan. 5, 2000

Related U.S. Application Data

(63) Continuation of application No. 08/980,032, filed on Nov. 26, 1997, now Pat. No. 6,013,449.

(51) Int. Cl.$^7$ ............................ C12Q 1/68; C12P 19/34; C12M 3/00; C07H 19/00; C07H 2/04
(52) U.S. Cl. ..................... 435/6; 435/91.1; 435/91.2; 435/283.1; 435/285.1; 435/287.1; 435/287.2; 536/22.1; 536/23.1; 536/23.2; 536/24.31; 536/24.32; 536/24.33
(58) Field of Search .................... 435/6, 91.1, 91.2, 435/283.1, 285.1, 287.1, 287.2; 536/23.1, 23.2, 23.5, 24.3, 24.31, 24.32, 24.33, 25.32; 702/19, 127, 20; 382/129

(56) References Cited

U.S. PATENT DOCUMENTS 5,998,147 A * 12/1999 Petit et al. ................ 435/6
6,013,449 A * 1/2000 Hacia et al. ............... 435/6

FOREIGN PATENT DOCUMENTS

| WO | WO 91/09226 | 6/1991 |
| WO | WO 95/11995 | 5/1995 |
| WO | 07171113 A2 * | 6/1996 |

OTHER PUBLICATIONS

Chee, M.S., et al., "Accessing genetic information with high–density DNA arrays," *Science* 274, 610–614 (1996).
Cronin, M.T., et al., "Cystic fibrosis mutation detection by hybridization to light–generated DNA probe arrays," *Hum. Mut.* 7, 244–255 (1996).
Easton, D.F., et al., "Genetic linkage analysis in familial breast and ovarian cancer," Results from 214 families, *Am. J. Hum. Genet.* 52, 678–701 (1993).
Fitzgerald, M.G., et al., "Germ–line BRCA1 mutations in Jewish and non–Jewish women with early–onset breast cancer," *N. Engl. J. Med.* 334, 143–149 (1996).
Ford, D., et al., "Risks of cancer in BRCA1–mutation carriers," *Lancet* 343, 692–695 (1994).
Friedman, et al., "Novel inherited mutations and expressivity of BRCA1 alleles, including the founder mutation 185delAG in Ashkenazi Jewish families," *Am. J. Hum. Genet.* 57, 1284–1297 (1995).
Hall, J., et al., "Linkage of early–onset familial breast cancer to chromosome 17q21," *Science* 250, 1684–1689 (1990).
Kozal, M.J., et al., "Extensive polymorphisms observed in HIV–1 clade B protease gene using high density oligonucleotide arrays," *Nature Med.* 2, 753–759 (1996).
Lipshultz, R.J., et al., "Using oligonucleotide arrays to probe genetic diversity," *BioTechniques* 19, 442–447 (1995).
Miki, Y., et al., "A strong candidate for the breast and ovarian cancer susceptibility gene BRCA1," *Science* 266, 66–71 (1994).
Narod, S., et al., "Familial breast–ovarian cancer locus on chromosome 17q12–q23," *Lancet* 338, 82–83 (1991).
Offit, K., et al., "Germline BRCA1 185delAG mutations in Jewish women with breast cancer," *Lancet* 347, 1643–1645 (1996).
Rowell, S., et al., "Inherited predisposition to breast and ovarian cancer," *Am. J. Hum. Genet.* 55, 861–865 (1994).
Shattuck–Eidens, D. et al., "A collaborative survey of 80 mutations in the BRCA1 breast and ovarian cancer susceptibility gene. Implications for presymptomatic testing and screening 1," *Am. Med. Assoc.* 273, 535–541 (1995).
Struewing, J.P., et al, "Detection of eight BRCA1 mutations in 10 breast/ovarian cancer families, including one family with male breast carrier," Am. J. Hum. *Genet.* 57, 1–7, (1995).
Struewing, J.P., et al, "The carrier frequency of the BRCA1 185delAG mutation is approximately 1 percent in Ashkenazi Jewish individuals," *Nature Genet.* 11, 198–200 (1995).
Hacia et al Nature Genetics vol. 14 pp. 441–447 1996.*

* cited by examiner

*Primary Examiner*—Jeffrey Siew
(74) *Attorney, Agent, or Firm*—Townsend and Townsend and Crew LLP

(57) ABSTRACT

The invention provides methods of analyzing a nucleic acid in a target sample for variant alleles. In such methods, a first-labelled control sample and a second-labelled target sample are hybridized to at least one set of probes. The control sample comprises a homozygous reference allele. The target sample comprises the homozygous reference allele, or variant alleles differing from the reference allele at a locus, or one variant allele differing from the reference allele at the locus and one reference allele. The probes in the probe set span the locus and are complementary to the reference allele. After hybridization the intensity of first and second label bound to each probe in the set is measured. This information is then used to indicate the presence of one variant allele and one reference allele, or the presence of two variant alleles in the target sample.

20 Claims, 5 Drawing Sheets

| T | +T |
|---|----|
| G | +G |
| C | +C |
| A | +A |

FIG. 1E

| WT | Δ1 | Δ2 | Δ3 | Δ4 | Δ5 |
|----|----|----|----|----|-----|

FIG. 2A
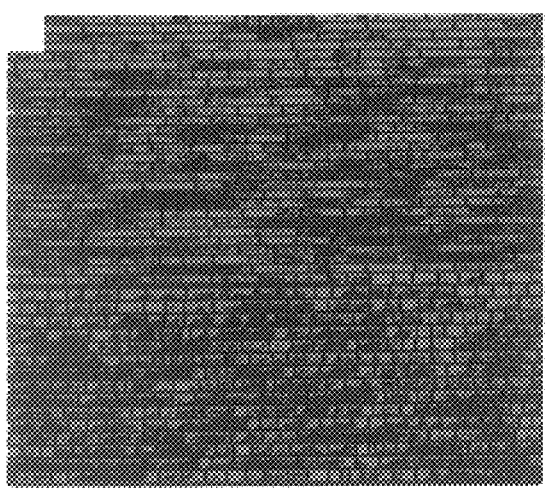
FIG. 2D  500 μm
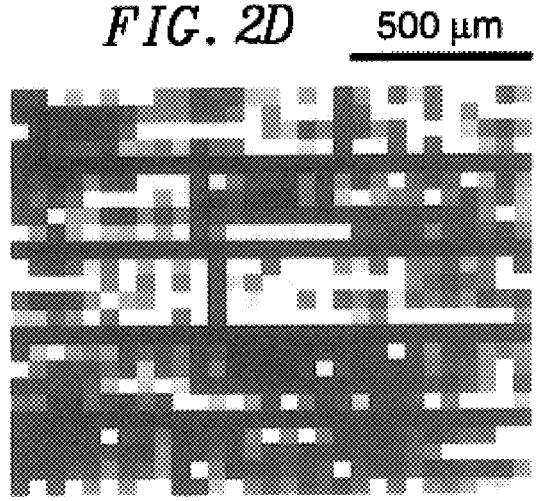
FIG. 2B
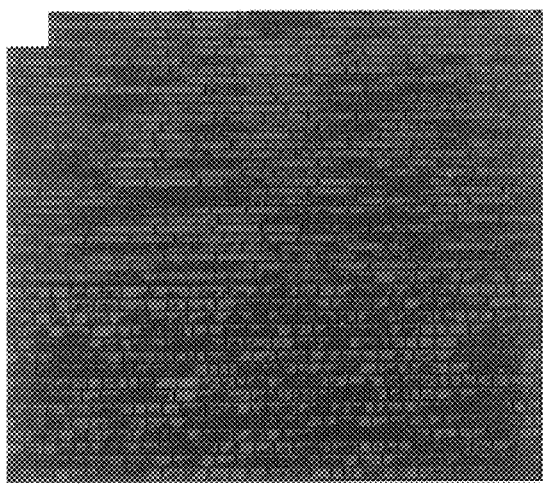
FIG. 2B  100 μm
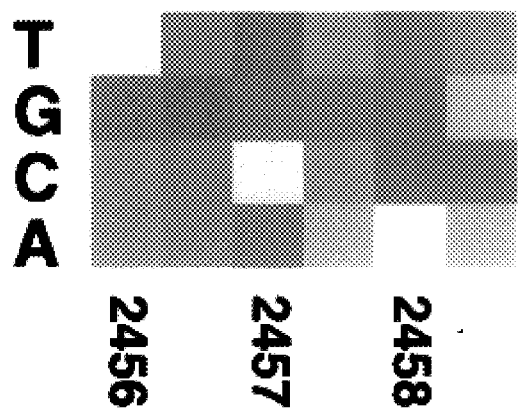
T G C A
2456  2457  2458
FIG. 2E
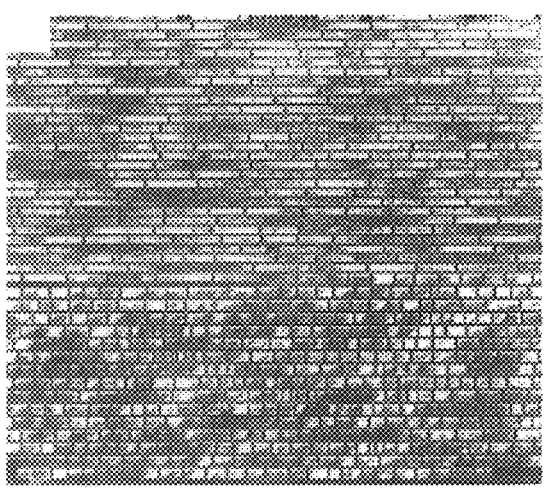
FIG. 2C

PROBE-BASED ANALYSIS OF HETEROZYGOUS MUTATIONS USING TWO-COLOR LABELLING

This application is a continuation of U.S. patent application Ser. No. 08/980,032, filed Nov. 26, 1997, now U.S. Pat. No. 6,013,449, which is incorporated by reference in its entirety.

STATEMENT OF GOVERNMENT INTEREST

The work described in this application was supported in part by CRADA IR43HG01431 from the US Government.

BACKGROUND

A variety of methods have been used to screen for mutations in genes. Usually, such methods begin with amplification of individual exons by DNA PCR or of the transcript by reverse transcription PCR. These methods include direct DNA sequencing, allele-specific probes, allele-specific primers and probe arrays. The design and use of allele-specific probes for analyzing polymorphisms is described by e.g., Saiki et al., Nature 324, 163–166 (1986); Dattagupta, EP 235,726, Saiki, WO 89/11548. Allele-specific probes are typically used in pairs. One member of the pair shows perfect complementary to a wildtype allele and the other members to a variant allele. In idealized hybridization conditions to a homozygous target, such a pair shows an essentially binary response. That is, one member of the pair hybridizes and the other does not.

An allele-specific primer hybridizes to a site on target DNA overlapping a polymorphism and primes amplification of an allelic form to which the primer exhibits perfect complementarity. See Gibbs, Nucleic Acid Res. 17, 2427–2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarity to a distal site. The single-base mismatch impairs amplification and little, if any, amplification product is generated.

Polymorphisms can also be identified by hybridization to ligonucleotide arrays as described in WO 95/11995 (incorporated by reference in its entirety for all purposes). Some such arrays include four probe sets. A first probe set includes overlapping probes spanning a region of interest in a reference sequence. Each probe in the first probe set has an interrogation position that corresponds to a nucleotide in the reference sequence. That is, the interrogation position is aligned with the corresponding nucleotide in the reference sequence, when the probe and reference sequence are aligned to maximize complementarily between the two. For each probe in the first set, there are three corresponding probes from three additional probe sets. Thus, there are four probes corresponding to each nucleotide in the reference sequence. The probes from the three additional probe sets are identical to the corresponding probe from the first probe set except at the interrogation position, which occurs in the same position in each of the four corresponding probes from the four probe sets, and is occupied by a different nucleotide in the four probe sets.

Such an array is hybridized to a labelled target sequence, which may be the same as the reference sequence, or a variant thereof. The identity of any nucleotide of interest in the target sequence can be determined by comparing the hybridization intensities of the four probes having interrogation positions aligned with that nucleotide. The nucleotide in the target sequence is the complement of the nucleotide occupying the interrogation position of the probe with the highest hybridization intensity.

WO 95/11995 also describes subarrays that are optimized for detection of a variant forms of a precharacterized polymorphism. A subarray contains probes designed to be complementary to a second reference sequence, which can be an allelic variant of the first reference sequence. The second group of probes is designed by the same principles as above except that the probes exhibit complementarity to the second reference sequence. The inclusion of a second group can be particular useful for analyzing short subsequences of the primary reference sequence in which multiple mutations are expected to occur within a short distance commensurate with the length of the probes (i.e., two or more mutations within 9 to 21 bases).

A further strategy for detecting a polymorphism using an array of probes is described in EP 717,113. In this strategy, an array contains overlapping probes spanning a region of interest in a reference sequence. The array is hybridized to a labelled target sequence, which may be the same as the reference sequence or a variant thereof. If the target sequence is a variant of the reference sequence, probes overlapping the site of variation show reduced hybridization intensity relative to other probes in the array. In arrays in which the probes are arranged in an ordered fashion stepping through the reference sequence (e.g., each successive probe has one fewer 5' base and one more 3' base than its predecessor), the loss of hybridization intensity is manifested as a "footprint" of probes approximately centered about the point of variation between the target sequence and reference sequence.

SUMMARY OF THE CLAIMED INVENTION

In some methods, the set of probes referred to above is a component of an array of immobilized probes, in which other probes may be present. In such methods, the entire array is hybridized to the first labelled control sample and the second labelled target sample. In some methods, the reference allele is at least 100 bases long and the probe set comprises at least 100 overlapping probes spanning the reference allele. In some methods, the target sample is prepared by amplifying nucleic acids from a patient with a pair of primers flanking the locus. In such methods, the target sample can be labelled in the course of amplification. The control sample can be similarly prepared by amplification of the reference allele from a pair of primers flanking the locus, and label can be similarly incorporated in the course of amplification.

In some methods, the array of probes also includes a econd set of probes spanning the locus and complementary to a elected variant allele. In such methods, the intensity of first and second label bound to each probe in the second probe set is determined and a normalized intensity ratio of first label to second label is calculated for each probe in the second set. An inverse normalized intensity ratio of probes in the second set overlapping the locus between 1 and 2 indicates that one copy of the selected variant allele is present in the target sample. An inverse normalized intensity ratio of probes in the second set overlapping the locus of over 2 indicates that two variant alleles are present. One or more additional probe sets can be includes in the array spanning the locus and complementary to one or more other variant alleles.

In some methods, the array of probes comprises first and second probe sets respectively comprising probes complementary to first and second strands of the reference allele, and third and fourth probe sets respectively comprising probes complementary to first and second strands of a selected variant allele. In such methods, the intensity of first and second label bound to each probe in the first and second sets is measured and a normalized intensity ratio of first label to second label for each probe in the first and second sets is caluculated. The mean intensity ratio is normalized to about one when the target sample comprises the homozygous reference allele. The presence of a target sample containing one reference and one variant allele is indicated if the mean normalized intensity ratio of probes in the first probe set overlapping the locus is between 1 and 2 and/or the mean normalized intensity ratio of probes in the second probe set overlapping the locus is between 1 and 2. The presence of a target sample comprising at least two variant alleles is indicated if the mean normalized intensity ratio of probes in the first probe set and/or the mean normalized intensity ratio of probes in the second probe sets overlapping the locus is greater than 2. The presence of a target sample containing one copy of the selected variant allele is indicated if the inverse mean normalized intensity ratio of probes in the third probe set overlapping the locus is between 1 and 2, and/or the inverse mean normalized intensity ratio of probes in the fourth probe set overlapping the locus is between 1 and 2. The presence of a target sample containing two copies of the selected variant allele is indicated if the inverse mean normalized intensity ratio of probes in the third probe set overlapping the locus is over 2, and/or the inverse mean normalized intensity ratio of probes in the fourth probe set overlapping the locus is over 2.

BRIEF DESCRIPTION OF THE FIGURES

FIGS. 1A–1E. Classes of Probe Array Oligonucleotides. Each position is interrogated with a total of 28 separate oligonucleotides, 14 each for the sense and antisense strands. All probes are 20-nt in length. FIG. 1A: Probes contain each of the four nucleotide substitutions nine bases from the 3' end of the oligonucleotide (one of these will represent the wild type sequence). FIGS. 1B and 1D: Insertion probes contain each of the four possible single nucleotide insertions nine bases from the 3' end of the oligonucleotide. FIGS. 1C and 1E: Deletion probes have 1–5-nt deleted nine bases from the 3' end of the oligonucleotide.

FIGS. 2A–2E. Chip Image Comparisons. FIG. 2A: Hybridization pattern of fluorescein reference target to an 1.28×1.28 cm array of 48,300 oligonucleotides (50 micron feature size) false colored in green. FIG. 2B: Hybridization pattern of phycoerythrin stained biotinylated RUL47 target false colored in red. FIG. 2C: Composite image of the false colored green and red images with areas of identical signal given in yellow. FIG. 2D: Magnification of the region surrounding the 2457 C→T mutation. FIG. 2E: Close-up of the probe sets surrounding the 2457 C→T mutation. BRCA1 cDNA nucleotide positions and identity of probes are labelled. The intervening columns represent different insertion probes at these positions. The normal sequence is T as 2456, C at 2457, and A at 2458. Details for the method of chip synthesis using light-directed oligonucleotide synthesis can be found in Fodor et al., *Science* 251, 767–773 (1991) and Pease et al., *Proc. Natn. Acad. Sci. U.S.A.* 91, 5022–5026 (1994). Briefly, DNA phosphoramidites bearing 5'-photolabile protecting groups are coupled to a solid silica substrate utilizing modified DNA synthesis protocols. Spatially addressable synthesis of oligonucleotide species is obtained through photolithographic techniques where selected oligonucleotides are photodeprotected on the chip surface for each coupling cycle. Combinatorial synthesis strategies may yield up to $2^n$ different oligonucleotide species in n synthesis cycles.

FIG. 3A: Sense strand ratios from 185-F15 (3875del4) FIG. 3B: Antisense strand ratios from 185-F15 (3875del4). A peak at the position of mutation is present on both strands.

FIG. 4A: Sense strand ratios from RUL47 (2457 C→T). FIG. 4B: Antisense strand ratios from RUL47 (2457 C→T). The nonsense mutation and five homozygous polymorphisms appear as distinct peaks on both strands FIG. 5. Data analysis algorithm flowchart. The number of analyzed patient samples containing exon 11 mutations which fulfill the indicated criteria of loss-of-signal or gain-of-signal essays is given.

DEFINITIONS

Figure 3A:
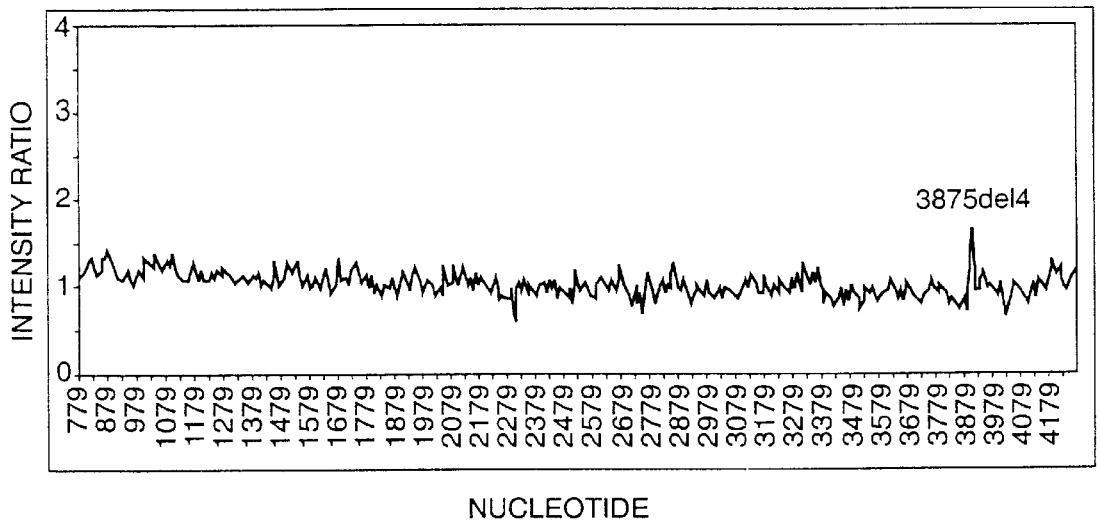
FIGS. 3A and 3B. Two-Color Loss of Signal Assay for a Deletion. Fluorescein-labelled reference and biotinylated targets were cohybridized to the array. To correct for reproducible differences in the hybridization efficiencies of reference and test targets, the ratio of fluorescein to phycoerythrin signal at each wild type position was normalized against ratios derived from a separate chip cohybridization experiment. Five data point moving averages of sense and antisense strand corrected ratios are plotted against nucleotide position.

An oligonucleotide can be DNA or RNA, or peptide nucleic acids, as described in Nielsen et al., *Science* 254, 1497–1500 (1991), or other nonnaturally occurring nucleic acid analog. Oligonucleotides can be single- or double-stranded. Oligonucleotides can be naturally occurring or synthetic, but are typically prepared by synthetic means. Oligonucleotides used in the invention are typically about 5–30 bases long, and often about 10–25 bases long. Hybridization probes are oligonucleotides capable of binding in a base-specific manner to a complementary strand of nucleic acid.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site refers to the area of the target DNA to which a primer hybridizes.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The allelic form occurring most frequently in a selected population is sometimes referred to as the wildtype form. Other allelic forms are designated as variant forms. Diploid organisms may be homozygous or heterozygous for allelic forms. A diallelic polymorphism has two forms.

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C. are suitable for allele-specific probe hybridizations.

Probes are typically designed to have perfect Watson-Crick base-pairing complementarity to a chosen sequence. Some probes may have leading or trailing sequences of noncomplementarity flanking a region of complementarity. The region of complementarity should be of sufficient length to allow specific hybridization to the chosen known sequence under stringent conditions.

DETAILED DESCRIPTION

I. General

The invention provides methods for analyzing nucleic acid(s) in a target sample to determine whether the target sample contains homozygous wildtype alleles, two or more variant alleles, or both wildtype and variant alleles (i.e., heterozygous alleles). Some methods also identify the nature of the variant alleles. The methods work by hybridizing a labelled control sample containing homozygous wildtype (also referred to as reference) allele together with the target sample, bearing a different label, to an array of probes. The array typically includes a set of probes with complementarity to the reference allele and spanning a site of potential variation between the reference allele and a variant allele. The hybridization intensity of control and target samples to each probe is separately determined from the differential labels, and a ratio of control to target signal is determined for each probe overlapping the site of potential variation.

If the target sample contains the same nucleic acid as the control sample (i.e., the target sample is the homozygous reference allele), then the ratio of signal intensities for each probe should be about, for example, 1. If it is not 1, a correction or normalization factor can be determined by which the observed ratio must be multiplied to reach unity when the target sample is the same as the control sample. Of course, the ratio of 1 discussed above, is merely exemplary and can vary depending on the concentration of the reference and target, the choice of labels, and the normalization algorithm used, among other factors.

If the target sample contains one or more variant alleles, the probes spanning the point of variation between a variant allele and the reference allele lack complementarity to the variant allele and hybridize less strongly to the variant allele than to the wildtype allele in the control sample. The ratio of hybridization intensities of control and target samples distinguishes between target samples in which one variant allele and one reference allele are present and in which two variant alleles are present. If the hybridization intensity ratio exceeds a first threshold value but less than a second threshold value (depending on, for example, concentration of reference and target, choice of labels and the normalization algorithm), one concludes that one reference allele and one variant allele is present in the target sample.

If the hybridization intensity ratio exceeds the second threshold value, one concludes that two variant alleles are present.

In one particular example, a normalized ratio of hybridization intensities of control sample to target sample to a probe complementary to the reference sequence of more than 2 is indicative of two variant alleles in the target sample. Such variant alleles both differ from the reference allele, but may or may not differ from each other. If the target sample contains one reference allele and one variant allele, an intermediate results occurs. That is, the reference allele in the target sample specifically hybridizes to probes spanning the point of variation, whereas the variant allele hybridizes to a lesser extent as a result of a mismatch. The net result is that the normalized ratio of hybridization intensities of control sample to target sample is between 1 and 2.

Accordingly, the ratio of hybridization intensities of the differentially labelled control and target samples allows characterization of the composition of the target sample as containing homozygous reference alleles, two variant alleles, or one variant allele and one wildtype allele.

Some methods also allow characterization of the nature of allelic variant(s) present in the target sample. In these methods, one or more additional probe sets are included in the arrays respectively showing complementarity to one or more selected variant alleles. If a target sample contains the selected variant allele in homozygous or heterozygous form, the target sample hybridizes to the additional probe set complementary to the selected allele more strongly than to the control sample. The inverse (i.e., reciprocal) ratio of normalized hybridization intensities of control to target samples indicates whether the selected variant allele is homozyous or heterozygous. For example, if the inverse standardized ratio is between 1 and 2, the target sample contains one reference allele and one copy of the selected variant allele. If the inverse standardized ratio is greater than 2, then the target sample is homozygous for the selected variant allele.

II. Reference Nucleic Acid

Virtually any known or partly known sequence can be selected as the reference or wildtype nucleic acid. The reference nucleic acid often encodes a gene or part of a gene.

Often the reference nucleic acid contains one or more known polymorphic sites. Typical reference nucleic acids of interest are human genes associated with genetic disease. Examples of such genes include BRCA-1, BRCA-2, p53, N-, C- and K-ras, cytochromes P450, CFTR, HLA classes I and II, and β-globin.

III. Sample Preparation

Polymorphisms are detected in a target nucleic acid from an individual being analyzed. For assays of genomic DNA, virtually any biological sample (other than pure red blood cells) is suitable. For example, convenient tissue samples include whole blood, semen, saliva, tears, urine, fecal material, sweat, buccal, skin, and hair. For assays of cDNA or mRNA, the tissue sample must be obtained from an organ in which the target nucleic acid is expressed. For example, if the target nucleic acid is a cytochrome P450, the liver is a suitable source.

Many of the methods described below require amplification of DNA from target samples. This can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202 (each of which is incorporated by reference for all purposes). Primers for amplification are selected to flank a region of interest in a target sample. For example, primers can be designed to be flank a known site of variation and a few bases on either side, or to flank an exon, or to flank a whole coding sequence or gene. In some methods, multiple regions of interest are amplified simultaneously by multiplex PCR. Nucleic acids in a target sample are usually labelled in the course of amplification by inclusion of one or more labelled nucleotides in the amplification mix. Labels can also be attached to amplification products after amplification e.g., by end-labelling. The amplification product can be RNA or DNA depending on the enzyme and substrates used in the amplification reaction.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

In some methods, control and target samples are prepared and obtained in parallel. That is, the samples are obtained from the same tissue or body fluid, and the same aliquot of sample is amplified under the same amplification conditions. Alternatively, the control sample can be obtained from an isolated supply of reference nucleic acid, and the final concentration adjusted to approximate to that of target nucleic acid. Control and target samples are distinguished in later steps by differential (i.e., two-color labelling). A variety of different fluorescent labels are available. For example, one sample can be labelled with fluorescein and the other with biotin, which can be stained with phycoerythrin-streptavidin after hybridization. Control and target samples can be diluted, if desired, prior to hybridization to equalize fluorescence intensities. For example, control and target nucleic acids can be diluted to a final concentration of 100 25 nM in a 25 $\mu$l solution of 30 mm $MgCl_2$ before application to probe arrays.

IV. Probe Arrays

Control and target samples are hybridized to arrays of oligonucleotide probes. Typically, the probes are immobilized to discrete cells of one or more supports, with each different probe occupying a separate cell. Some arrays contain more than one set of probes, each set serving a different role in the analysis. In this situation, the different probe sets can all be on the same support, but commonly some of the probe sets are on one support and other probe sets are on another support.

Typically, an array contains one probe set with probes that tile a region of interest in a reference allele. The length of the region of interest can vary widely from a single base, to 10 bases, 100 bases, 1000, 10,000, 100,000 or 1,000,000 bases. Tiling means that the probe set contains overlapping probes which are complementary to and span a region of interest in the reference allele. For example, a probe set might contain a ladder of probes, each of which differs from its predecessor in the omission of a 5' base and the acquisition of an additional 3' base. If the location of a polymorphic site is known, the probe set typically contains at least some probes that overlap the site of potential variation, and other probes that are complementary to immediately flanking regions. However, some probe sets contain only probes that overlap the site of variation. Some probe sets contain probes that span most or all of a gene or the coding region(s) thereof. The probes in a probe set may or may not be the same length. The number of such probes can vary widely from about 1, 5, 10, 20, 50, 100, 1000, to 10,000 or 100,000.

Some arrays contain an additional probe set, designed according to the same principles as the first probe set, except that the probes in the two probe sets are complementary to the two different strands (e.g., sense and antisense strands) of the wildtype nucleic acid sequence. Although, in theory, the two probe sets should hybridize to their respective complementary strands in a double-stranded target sequence to the same extent, base-composition effects sometimes result in different hybridization intensities from the two probe sets. Combined analysis of both probe sets increases the accuracy of the analysis.

Some arrays contain one or more further probe sets designed according to the same principles as the previous probe sets, except that the further probe sets are designed to be complementary to a selected variant form of the reference allele. At least one such further probe set can be designed for each possible variant allele of the reference sequence.

Optionally two further probe sets can be designed for each possible variant allele of the reference sequence, the two probe sets respectively designed to exhibit complementarity to first and second strands of the variant form.

The further probe sets designed to be complementary to variant alleles give reciprocal hybridization patterns to the probe sets designed to be complementary to the reference allele. That is, a target sample containing one or both copies of a selected variant allele hybridizes to probes complementary to the selected variant allele and overlapping the site of variation detectably more strongly than does a control sample containing a homozygous reference allele. For example, using the same preset threshold values for hybridization intensities as above, if the inverse of the normalized hybridization intensity of the control sample to the target sample is greater than 2, the presence of homozygous variant alleles is suggested in the target sample.

If the inverse of the normalized hybridization intensity is between 1 and 2, the presence of heterozygous wildtype and variant alleles is indicated.

Some arrays contain one or more additional probe sets designed according to the same principles as any of the previous probe sets except using a different length of probe. Including alternative probe lengths, such as 17, 20, and 25 bases on a substrate increase accuracy not only by reproducing variations in normalized hybridization intensity ratios but also by causing predictable changes in signal widths (i.e., contiguous probes showing altered intensity ratios relative to other probes in a set). Hybridization intensities from longer probes generates broader signals while data from shorter probes generates sharper signals. In general, if a variant allele contains a single base substitution relative to a reference allele, and a set contains probes stepping along the reference allele in units of one base, then n probes overlap the point of variation. These n probes show elevated normalized hybridization intensity ratios of control sample to target sample, when the target sample contains one or two copies of a variant allele.

The above probe sets are suitable for analysis of a single reference allele and variants thereof. However, the same principles can be applied for parallel analysis of any number of reference alleles and corresponding variants. For example, to analyze ten different reference alleles and corresponding variants from different areas of the human genome, one needs at least ten probe sets as described above respectively complementarity to the ten reference alleles. Additional probe sets containing probes complementary to first and second strands of reference alleles, and or first and second strands of selected variant forms can also be included.

In addition to the probe sets described above, arrays can contain still further probe sets that serve to analyze target samples by independent means. Examples of such probe sets are described in WO 95/11995. In addition, control probes can be included that serve to orient the chip, or gauge hybridization background, which can include target sequence nonspecifically bound to a support bearing the probes, or determine completeness of amplification.

Arrays of probe immobilized on supports can be synthesized by various methods. A preferred method is VLSIPS™ (see Fodor et al., *Nature* 364, 555–556 (1993); McGall et al., U.S. Ser. No. 08/445,332; U.S. Pat. No. 5,143,854; EP 476,014), which entails the use of light to direct the synthesis of oligonucleotide probes in high-density, miniaturized arrays. Algorithms for design of masks to reduce the number of synthesis cycles are described by Hubbel et al., U.S. Pat. No. 5,571,639 and U.S. Pat. No. 5,593,839. Arrays can also be synthesized in a combinatorial fashion by delivering monomers to cells of a support by mechanically constrained flowpaths. See Winkler et al., EP 624,059. Arrays can also be synthesized by spotting monomers reagents on to a support using an ink jet printer. See id.; Pease et al., EP 728,520.

V. Analysis of Hybridization Patterns

After hybridization of control and target samples to an array containing one or more probe sets as described above and optional washing to remove unbound and nonspecifically bound probe, the hybridization intensity for the respective samples is determined for each probe in the array. For fluorescent labels, hybridization intensity can be determined by, for example, a scanning confocal microscope in photon counting mode. Appropriate scanning devices are described by e.g., Trulson et al., U.S. Pat. No. 5,578,832; Stern et al., U.S. Pat. No. 5,631,734, and are available from Affymetrix, Inc. under the GeneChip trademark.

A normalized hybridization ratio of the intensity of the control sample to the target sample can be calculated for each probe in the array. The ratio is typically normalized using two substrates bearing identical arrays of probes. One substrate is hybridized to two aliquots of control sample, which are identical except that the two aliquots bear different labels. A ratio of hybridization intensities for the two labels is calculated for each probe. If the ratio is not unity, a normalization factor is calculated to reduce the ratio to unity. Control and target samples bearing different labels are then applied to the second chip, and the ratio of the two label intensities is determined for each probe. The raw ratio for each probe is then multiplied by the normalization factor calculated for that probe to give a normalized ratio of control to target signal for each probe.

Normalized intensity ratios of probes that overlap a site of variation between a variant allele and a wildtype allele are used to determine the composition of the target sample. If the location of the site of variation is known, then one also knows which probes overlap the site of variation. For example, if the site of variation is a single-base substitution, and a probe set contains a series of probes of length n stepping across the site of variation in units of one base, then n probes overlap the site of variation. If the site of variation is a single-base deletion, then n−1 probes overlap the site of variation, and if the site of variation is a single-base insertion, then n+1 probes overlap the site of variation.

If the site of variation is not known, it can be identified from the presence of a contiguous subset of probes with altered normalized probe intensities relative to other probes in a probe set. That is, if one plots normalized intensity ratios of control and target samples versus probe for a ladder of probes tiling along a reference allele, and the target sample contains one or more copies of a variant form of the reference allele, one sees a subset of contiguous probes (i.e., a spike if the intensity ratio is control sample to target sample; a footprint if the intensity ratio is target sample to control sample) with significantly altered normalized probe intensity relative to the other probes in the probe set. The probes having altered normalized intensity ratio overlap the site of variation between the wildtype allele and the variant allele.

The mean of the normalized hybridization ratio of probes overlapping a site of variation indicates the composition of the target sample. For probe sets showing complementarity to a reference allele (either strand), a mean normalized hybridization intensity ratio greater than 2 indicates that the target sample contains two copies of a variant allele, and a mean normalized hybridization intensity ratio between 1 and 2 indicates that the target sample contains one wildtype allele and one variant allele. For probe sets showing complementarity to a selected variant allele, an inverse (i.e., reciprocal) mean normalized hybridization intensity ratio greater than 2 indicates that the target sample contains two copies of the selected variant allele, and an inverse mean normalized hybridization ratio between 1 and 2 indicates that the target sample contains one copy of the selected variant allele and one copy of the wildtype allele.

When probe sets are included for both strands of a reference allele, mean normalized hybridization intensity ratios of probes overlapping the site of variation between the reference allele and a variant allele are determined as before. If the mean normalized hybridization intensity ratios for both probe sets are greater than two, the data from each set reinforces the other, and one concludes that the target sample contains two variant alleles. Likewise, if the mean normalized hybridization intensity ratios for both probe sets are between 1 and 2, then the target sample contains one variant allele. If one probe set gives a mean normalized hybridization intensity ratio between 1 and 2, and the other probe set gives a mean normalized hybridization intensity ratio above 2, then it is likely that the target sample contains at least one copy of a variant allele. However, further investigation is warranted (e.g., using other array designs) or by cloning and dideoxysequencing to resolve the ambiguity. Data from probe sets for both strands of a selected variant allele are analyzed in a similar fashion to determine whether one or both copies of the variant allele are present, or whether further investigation by other means is warranted.

Some methods employ a two-tiered strategy for analysis of a target sample. The first level of analysis employs a substrate containing probe set(s) complementary to one or more unrelated reference alleles. Preferably, two probe sets are included for each reference allele designed to be complementary to the respective strands of the allele. Hybridization of control and target (e.g., patient) samples to such an array and analysis of mean normalized hybridization intensity ratios reveals the existence of one or more variant alleles and the approximate location of the point of variation. The same samples can then be hybridized to a second substrate containing probe sets complementarity to different possible variant alleles at the sites of suspected variation from the reference allele. Identification of a probe set showing a decreased ratio of control to target sample (or increased ratio of target sample to control) reveals the nature of the variant alleles present in the sample.

To illustrate one might have a first substrate that contains probe sets complementary to the reference form of one hundred different genes. Analysis of the hybridization intensity might indicate the likely existence of variant alleles in just one of these genes. One then hybridizes the control and target samples to a second substrate, which contains several probe sets respectively complementary to the different allelic forms of this gene. If the first level of analysis indicates the target sample contains allelic variants in two genes, one can then hybridize the control and target samples to still another substrate containing probe sets showing complementarity to different allelic forms of the further gene.

EXAMPLES

Germline mutations in BRCA1 are present in 50–60% of kindreds with breast and ovarian cancer, and may account for approximately 2–5% of all breast cancer cases in the general population (Hall et al., *Science* 250, 1684–1689 (1990), Narod et al., *Lancet* 338, 82–83 (1991), Easton et al. *Am. J. Hum. Genet.* 52, 678–701 (1993), Rowell et al., *Am. J. Hum. Genet.* 55, 861–865 (1994)). Heterozygous carriers are markedly predisposed to early onset breast and ovarian cancer, and are also at moderately increased risk of developing colon and prostate cancer (Ford et al., *Lancet* 343, 692–695 (1994)). The protein coding region of BRCA1 contains 5,592-bp in 22 coding exons spread over 100-kb of genomic DNA (Miki et al., *Science* 266, 66–71 (1994)). Over 111 unique BRCA1 mutations distributed throughout the gene have been described in the literature (Shattuck-Eidens et al., *Am. Med. Assoc.* 273, 535–541 (1995) and (Breast Cancer Information Core Database located on the World Wide Web at http://www.nchgr.nih-gov/Intramural-research/Lab-transfer/Bic/.)). Most of these are frameshift, nonsense, or splice mutations resulting in a disruption of the normal reading frame. Except for the Ashkenazi Jewish population, where two mutations account for the majority of BRCA1 alterations (Struewing et al., *Am J. Hum. Genet.* 57, 1–7 (1995); Struewing et al., *Nature Genet.* 11, 198–200 (1995); Tonin et al., *Am. J. Hum. Genet.* 57, 189 (1995); Friedman et al., *Am. J. Hum. Genet.* 57, 1284–1297 (1995); FitzGerald et al., *N. Engl. J. Med.* 334, 143–149 (1996); Offit et al., *Lancet* 347, 1643–1645 (1996)), allelic heterogeneity confounds the ability to identify BRCA1 mutation carriers by methods (such as allele-specific oligonucleotide [ASO] hybridization) which detect only a finite set of previously described mutations.

I. Methods (a) PCR from Genomic DNA and RNA Target Preparation

PCR reactions were performed on genomic samples using the EXPAND™ Long Range PCR Kit (Boehringer Mannheim) with primers 11FT3 5'-ATTAACCCTCAC TAAAGGGAATTAAATGAAAGAGTATGAGC-3' (SEQ ID NO:1) and 11RT7 5-TAATACGACTCACTATAGG GAGTGCTCCCAAAAGCATAAA-3' (SEQ ID NO:2) containing T3 and T7 RNA polymerase promoter sequences respectively. In vitro transcription reactions from these exon 11 amplicon templates were performed in 10 µl reaction volumes using T3 RNA polymerase transcription buffer (Promega), 0.7 MM of ATP, CTP, GTP, and UTP, 10 MM DTT, 0.7 MM fluorescein-12-UTP or 0.15 MM biotin-16-UTP (Boehringer Mannheim) for reference and test samples respectively, and 1OU T3 or T7 RNA polymerase as indicated.

(b) Target Preparation and Analysis

Reference template was generated from PCR amplification of exon 11 from a BRCA1 cDNA clone. Reference and test sample transcription products were diluted to a final concentration of 100 nM in a 25 µl solution of 30 mm MgCl$_2$. The reaction was incubated at 94° C. for 70 minutes to fragment targets (Lipshutz, et al., *BioTechniques* 19, 442–447 (1995); Kozal, et al., *Nature Med.* 2, 753–759 (1996)). Cofragmented targets were diluted 1/100 into a 300 pl volume of hybridization buffer (3 M TMAC-Cl (tetramethylammonium chloride), 1×TE pH 7.4, 0.001% Triton X-100, 1 nM 5'fluorescein-labelled control oligonucleotide 5'-CGGTAGCATCTTGAC-3')(SEQ ID NO:3). This control oligonucleotide is designed to hybridize to specific surface probes to aid in image alignment. Target was hybridized with the chip in a 250 µl volume for 4 hours at 35° C. The chip surface was washed with 10 ml of wash buffer (6×SSPE, 0.001% Triton X-100) and stained with phycoerythrin-streptavidin conjugate (Molecular Probes) (2 µg/ml in wash buffer) for 5 minutes at room temperature. The chip was washed with 10 ml of wash buffer and scanned as described (Lipshutz et al., *BioTechniques* 19, 442–447 (1995); Kozal et al., *Nature Med.* 2, 753–759 (1996)). Hybridization signals were detected by a photomultiplier tube using 515–545 nm bandpass and 560 nm longpass emission filters for fluorescein reference (green) and biotin test (red) samples respectively (Cronin et al., *Hum. Mut.* 7, 244–255 (1996); Chee et al., *Science* 274, 610–614 (1996)).

(c) Data Analysis

Photomultiplier output signal was converted into proportional spatially addressed pixel values using GeneChip Software (Affymetrix) to create a digitized fluorescence image. The relative contributions of the reference and test targets to each probe signal were extracted from each set of experimental green reference and red test images and imported into a Microsoft Excel 7.0a worksheet. The ratio of reference and test signals for each wild type probe was quantitated and compared to the same ratios measured from an identical experiment performed on a different test sample. The ratios of the reference/test ratios derived from the two separate experiments were plotted against nucleotide position to generate loss of signal data, as in FIGS. 3A and 3B and FIG. 4A and 4B. It is necessary to compare reference/test wild type probe signal ratios from separate experiments to generate a stable baseline as the baseline generated by plotting reference/test wild type probe signal ratios generated from a single chip against nucleotide position was not sufficiently stable to permit data analysis.

(d) Dideoxysequencing Analysis

Four pairs of PCR primers (P1M13+5'-GTTTCCCAGTCACACGGAATTAAATGAAAG AGTATGAGC-3' (SEQ ID NO:4) and PIM13-5'-AGGAAACAGCTATGACCATGTGAGGGGACGCTCT TG-3' (SEQ ID NO:5), P2M13+5'-GTTTCCCAGTCA CACGTTGGGAAAACCTATCGGAA-3' (SEQ ID NO:6) and P2M13 5'-AGGAAACAGCTATGACCATCTTTGGGG TCTTCAGCA-3' (SEQ ID NO:7), P3M13+5'-GTTTCCCAGTCACACGTGTTCAAATACCAGTGAAC TTA-3' (SEQ ID NO:8) and P3M13-5'-AGGAAACAG CTATG ACCATGGAGCCCACTCATTAGTAC-3' (SEQ ID NO:9), P4M13+5'-GTTTCCCAGTCACACGCCAAGT ACAGTGAGCACAATTA-3' (SEQ ID NO:10) and P4M13-5'-AGGAAACAGCTATGACCATGTGCTCCC AAAAGCATAAA-3'(SEQ ID NO:11)) were designed to generate four partially overlapping amplicons which cover the entire sequence of exon 11 and contain M13 forward and reverse sequences at the 5'-end of either strand Depending on region to be analyzed one of the four amplicons was generated from the appropriate genomic sample using the EXPAN™ Long Range PCR kit (Boehringer Mannheim) with the recommended protocol. Dye primer dideoxysequenciong reactions were performed using AmpliTaq DNA Polymerase FS kit (Perkin Elmer) with the suggested protocol and either M13 forward or M13 reverse DYEnamic™ energy transfer dye primers (Amersham Life Science).

II. Results (a) Design of Oligonucleotide Array

We examined the ability of a DNA-chip based assay to detect heterozygous mutations in the 3.45-kb BRCA1 exon 11, which contains approximately 60% of the BRCA1 coding region. Families of over 96,600 oligonucleotides were designed to detect all possible single base substitutions, single base insertions, and 1–5-bp deletions on both strands. Four 20-nt long probes, substituted with one of the four nucleotides in the central position, interrogate the identity of each nucleotide (FIG. 1A and 1D). Four 20-nt long insertion probes containing the possible single base insertions at the central position query for the presence and identity of an insertion (FIG. 1B and 1D). Likewise five 20-nt long deletion probes query for the presence and identity of all possible 1–5-bp deletions (FIG. 1C). Allele specific oligonucleotides complementary to other previously described mutations not included in the above classes also may be easily incorporated.

This chip design provides redundant information which contributes to sensitivity and specificity. Ideally, a heterozygous, mutation in a patient sample should result in 1) a "gain of signal" increase in hybridization to an oligonucleotide representing a perfect match to the mutant sequence, provided it is represented on the chip; and 2) a 50% "loss of signal" intensity (relative to a normal control) for the family of wild type oligonucleotide probes that query the position of the mutation. Due to the complexity of the hybridization reaction, specific mutations may only fulfill a subset of these ideal criteria. Thus, we define an algorithm which maximizes sensitivity and specificity in the analysis of this intentionally redundant data.

(b) Two-color Analysis System

Wild type fluorescein-labelled ("green") reference and biotinylated (stained with a phycoerythrinstreptavidin "red" conjugate after hybridization) RNA test targets were competitively co-hybridized to the array with the relative binding to all probes measured. The ratio of reference and test targets occupancy to each of the 96,600 oligonucleotides in the array was used to detect sequence differences between the two samples. RNA-based targets were used in favor of DNA-based targets since they showed superior hybridization fidelity and signal strength in this system.

(c) Gain of Signal Analysis

Mutant substitution, insertion, and deletion probes should detect sequence changes through a gain of hybridization signal in the test target, since wild type target generally should not hybridize strongly to them. An example using this analysis to detect heterozygous base substitutions is given in FIGS 2A–2E. The hybridization pattern of the reference is shown in green (FIG. 2A) while the hybridization pattern of sample RUL47 containing a 2457 C→T nonsense mutation is shown in red (FIG. 2B). These images were superimposed with the areas of identical signal given in yellow (FIGS. 2C and 2D). The region of the array corresponding to the mutant allele is shown in FIG. 2E. Only the wild type allele 2457 "C" probe hybridized with the reference target. In contrast, the heterozygous mutant target hybridized to both the wild type allele 2457 "C" probe as well as the mutant allele 2457 "T" probe, resulting in a red signal at the position of the mutation.

(d) Loss of Signal Analysis

Figure 3B:
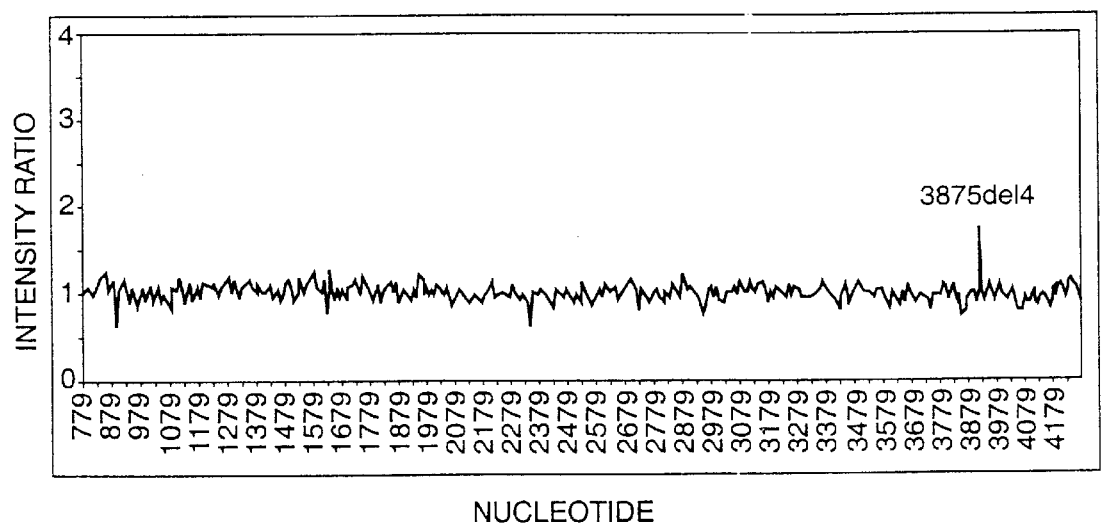

Two-color loss of signal assays are a second analytical means of detecting sequence differences between samples. Localized changes in hybridization signal ratios may reflect different stoichiometries of wild type alleles in the hybridization solution, and thus potential heterozygous sequence differences between the two samples. A corrected ratio (see legend to FIGS. 3 and 3B) of reference sample and test sample binding to wild type sequencing probes for each strand can be plotted against nucleotide position. Regions of identical sequence should be close to a value of 1.0, while regions of sequence differences should show a peak centered near the point of mutation. For a point mutation, this width should be about 20-bp wide; for a deletion of n-bp it is expected to be approximately (n+20)-bp in width. This "width property" of true peaks helps to distinguish them from noise. An example showing detection of the 3875del4 mutation on both strands is shown in FIGS. 3A and 3B. Ideal heterozygous mutations should produce peaks with a value of about 2.0, reflecting the two wild type alleles in the reference compared to the single wild type allele in the mutant heterozygote sample. Any crosshybridization of the mutant allele to the wild type probe will reduce this ratio closer to 1.0. In practice, a cut-off of 1.2 was found to represent a good threshold.

Figure 4A:
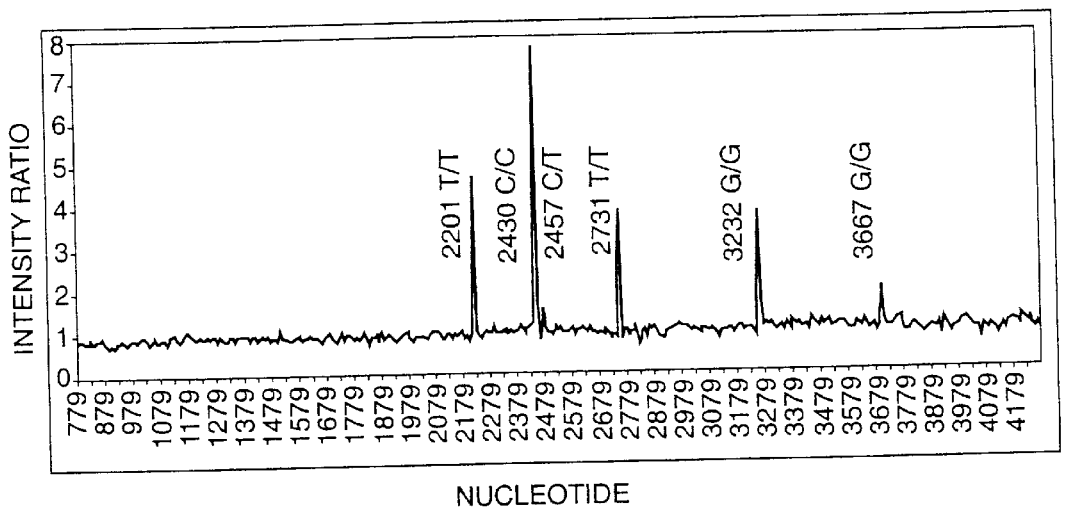
FIGS. 4A and 4B. Two-Color Loss of Signal Assay for a Nonsense Mutation.
Figure 4B:
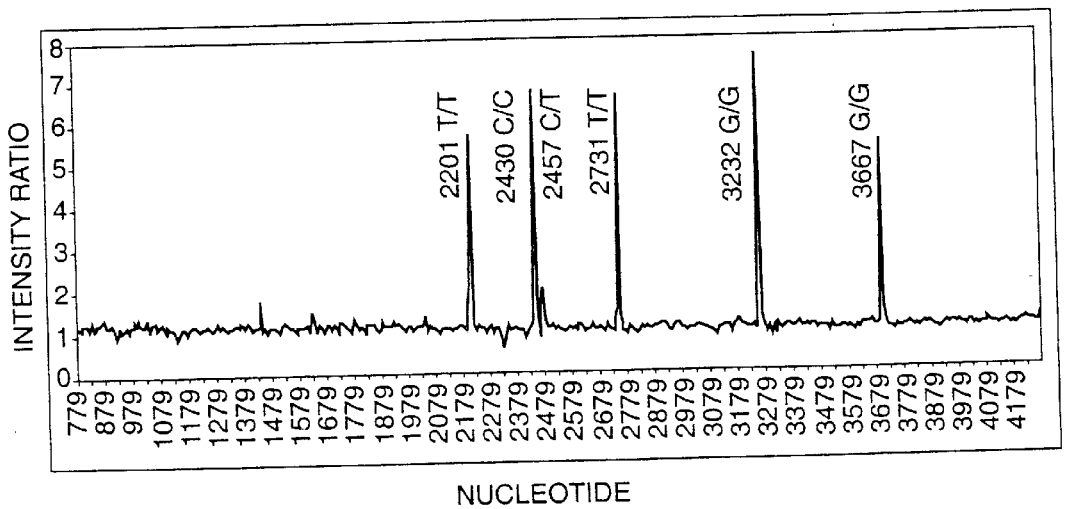

Homozygous sequence differences will produce larger peaks. In FIGS. 4A and 4B for example, six separate peaks were observed for each strand of sample RUL47. One of these (the smallest) detects the heterozygous 2457 C→T nonsense mutation. The other five strong peaks correspond to five polymorphisms 2201 T/T,21430 C/C, 2731 T/T, 3232 G/G, and 3667 G/G found in sample RUL47 in the homozygous state. These variants have been previously described and are in strong disequilibrium with each other.

(e) Application to Multiple Different BRCA1 Mutations

A summary of the results of two-color gain and loss of signal analysis experiments for 15 known exon 11 BRCA1 mutations are given in Table 1. These represent all of the genomic DNA samples available to us which contain known alterations in this exon. In addition, twenty control samples from individuals without a known family history of breast cancer were evaluated to ascertain the specificity of the assay. Seven previously reported polymorphisms were detected along with a previously unreported heterozygous base substitution 1606 G→A (Arg496His) found in sample RUL57, which was confirmed by dideoxysequencing. Seven of pathologic mutations (2314del5, 2457C→T, 2804delAA, 3286delG, 3867G→T, 3937insG, and 3986delAA) were detected in completely optimal fashion with clear gain of signal and loss of signal results on each strand. For the other mutations, the sensitivity of any particular assay on one or both strands was imperfect. For example, while the 3875del4 mutation was readily detected with the loss of signal assay (FIGS. 3A and 3B), the gain of signal assay failed to give a distinct signal, presumably because of strong wild type target cross-hybridization at this location. Gain of signal assays based upon insertion and deletion probes were also capable of generating a significant number of false positive signals using this criteria, whereas the loss of signal assay was more robust.

TABLE 1

Sensitivity of mutation detection in patient samples with germline mutations in BRCA1 exon 11

| Mutation | Sample | Gain of Signal[a] | | Loss of Signal[b] | | Mutation Identification[c] |
|---|---|---|---|---|---|---|
| | | Coding | Non-coding | Coding | Non-coding | |
| 1128insA | ST750 | − | − | − | − | No |
| 1294del40 | 624-F32 | na | na | + | + | Yes |
| 1323delG | 3295 | − | + | + | − | Yes |
| 2294delG | ST755 | − | − | + | + | Yes |
| 2314del5 | RUL57 | + | + | + | + | Yes |
| 2457C−>T | RUL47 | + | + | + | + | Yes |
| 2804delAA | MOC52 | + | + | + | + | Yes |
| 3121delA | ENG9 | + | + | − | + | Yes |
| 3286delG | ENG7 | + | + | + | + | Yes |
| 3452del4 | ENG5 | − | − | + | + | Yes |
| 3600del11 | 3265 | − | − | + | + | Yes |
| 3867G−>T | 808-F161 | + | + | + | + | Yes |
| 3875del4 | 185-F15 | − | − | + | + | Yes |
| 3937insG | RUL77 | + | + | + | + | Yes |
| 3986delAA | ENG3 | + | + | + | + | Yes |

[a]+ indicates that the mutant probe has an intensity 1.2X or greater than the corresponding wild type probe − indicates that the mutant probe has an intensity less than a factor of 1.2X the corresponding wild type probe; na indicates data not available; [b]+ indicates a distinct peak at the mutant position − indicates the absence of a distinct peak at the mutant position; [c]mutation detection algorithm defined in text.

(f) Algorithm for Combining Hybridization Data from Multiple Probe Sets

Figure 5:
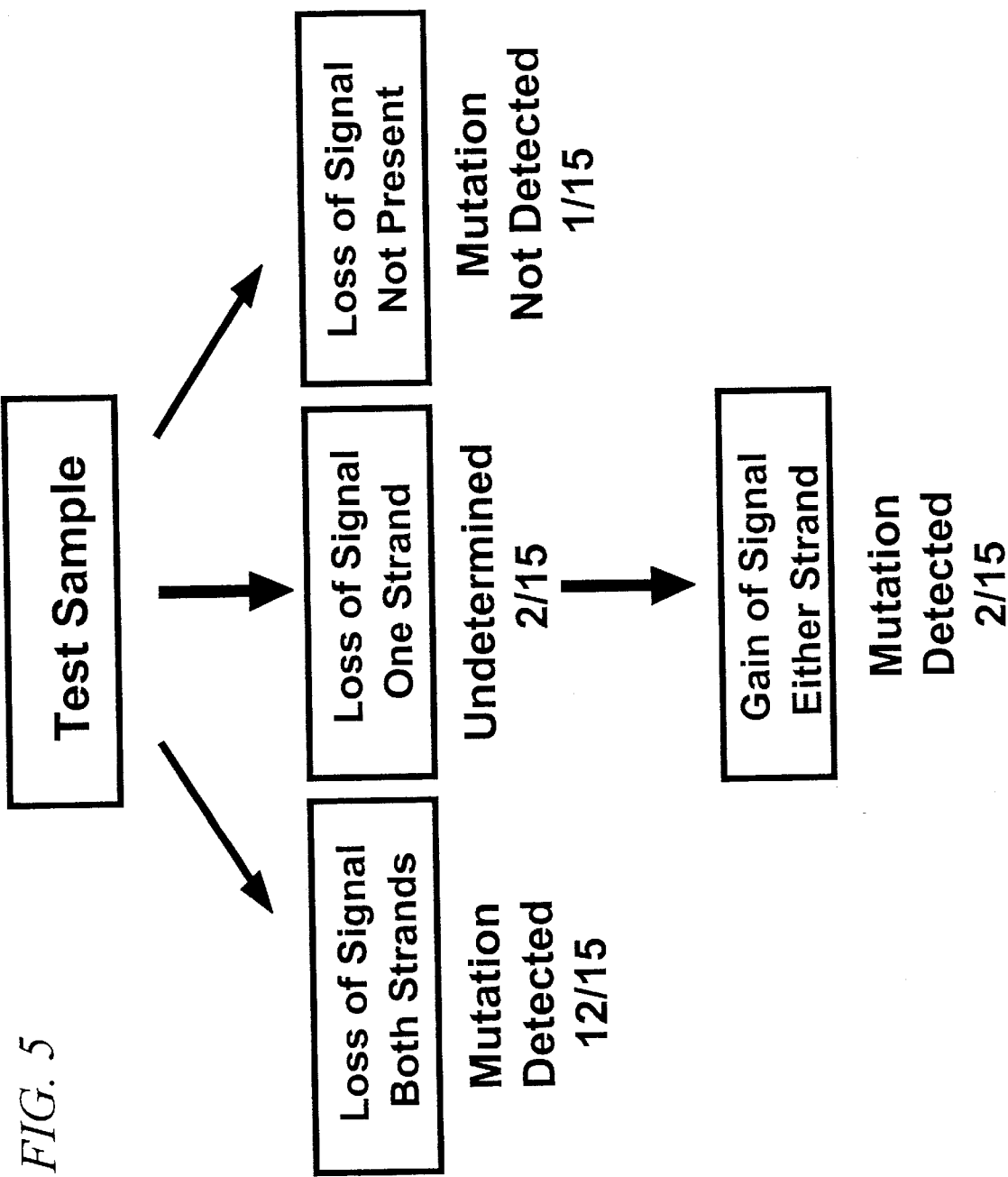

These observations resulted in the following algorithm for interpreting chip hybridization data (FIG. 5): First examine the loss of signal data. If a peak of width>20-bp is found in the same position on both strands, a sequence alteration is almost certainly present. We encountered no false positives of this sort in examining 3.45-kb of BRCA1 exon 11 sequence in 15 patients and 20 control samples (a total of>120-kb of BRCA1 sequence). Twelve of the 15 patient mutations in Table 1 were immediately detectable by this strategy, and the precise mutation could then be identified in seven of them by examining the gain of signal data. In ambiguous cases where there is a loss of signal on one strand but not the other, the gain of signal data can still lead to accurate mutation detection. Two samples show loss of signal (of≧20-bp) on one strand but not the other. In one of these (ENG9, 3121delA) there is a specific gain of signal for the appropriate oligonucleotide on both strands, whereas the other (3295, 1323delG) reveals this gain of signal on one strand only. In 20 control samples, a specific loss of signal on one strand was never accompanied by a confirmatory gain of signal on either strand. Since this criterion does not appear to result in false positives, we scored both ENG9 and 3295 as having been correctly identified as mutation-bearing. Only one of the fifteen samples (ST750, 1128insA), which showed neither a specific gain or loss of signal on either strand, was scored as a false negative in the current assay. That mutation results from the expansion of a poly (dA)-,(dT) tract from 7-nt to 8-nt in length, and would be predicted to be particularly difficult to detect. Two other samples that putatively contained the mutations 2086insG and 2035 T→A did not generate specific loss or gain of signal on either strand. Dideoxysequencing analysis confirmed that these samples were of wild type sequence in this region. Thus with the current algorithm the sensitivity of the method is 93% and the specificity is 100%.

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

What is claimed is:

1. A method of analyzing a nucleic acid in a target sample, comprising:

(a) hybridizing a first-labelled control sample comprising a homozygous reference allele, and a second-labelled target sample comprising the homozygous reference allele, or variant alleles differing from the reference allele at a locus, or one variant allele differing from the reference allele at the locus and one reference allele, to at least one set of probes spanning the locus and complementary to the reference allele, wherein the first and second labels are different;

(b) measuring the intensity of first and second label bound to probes in the probe set; and (c) determining a normalized intensity ratio of first label to second label for probes in the probe set, wherein the value of the ratio relative to one or more threshold values is an indicator of whether only reference alleles, only variant alleles or both reference and variant alleles are present in the target sample.

2. The method of claim 1, wherein the set of probes is immobilized on a substrate as part of an array of probes, and the hybridizing step comprises hybridizing the first-labelled control sample and the second-labelled target sample to the array of probes.

3. The method of claim 2, further comprising washing the substrate with a wash solution to remove unbound alleles.

4. The method of claim 1, wherein there are at least 10 probes within each probe set.

5. The method of claim 3, wherein there are at least 100 probes within each probe set.

6. The method of claim 4, wherein there are at least 10,000 probes within each probe set.

7. The method of claim 2, where in t he set of probes contains probes that span the locus and probes that hybridize to regions that flank the locus but do not span the locus.

8. The method of claim 2, wherein the set of probes contains only probes that span the locus.

9. The method of claim 2, wherein the reference allele comprises a gene and the set of probes comprises overlapping probes that span the gene.

10. The method of claim 2, wherein the reference allele comprises a gene and the set of probes comprises overlapping probes that span the coding sequence of the gene.

11. The method of claim 2, wherein the probes within the set of probes are the same length.

12. The method of claim 2, wherein the probes within the set of probes are different lengths.

13. The method of claim 2, wherein the array of probes comprises a second set of probes, the first and second probe sets respectively comprising probes complementary to first and second strands of the reference allele and the hybridizing step comprises hybridizing the control sample and the target sample to the second probe set, and the method further comprises (d) measuring the intensity of first and second label bound to probes in the second probe set; and (e) determining a normalized intensity ratio of first label to second label for probes in the second probe set, wherein the value of the ratio for the second probe set relative to one or more threshold values is an indicator of whether only reference alleles, only variant alleles or both reference and variant alleles are present in the target sample.

14. The method of claim 13, wherein if steps (c) and (e) give differing indications, then the method further comprises sequencing at least one of the alleles within the target sample.

15. The method of claim 2, wherein the first-labeled control sample comprises a plurality of different homozygous reference alleles;

the second-labeled target sample potentially comprises (i) one or more of the homozygous reference alleles, or (ii) one or more corresponding variant alleles, each variant allele differing from one of the reference alleles at a locus, or (iii) one or more reference allele and its corresponding variant allele;

the probe array comprises a plurality of probe sets, each probe set comprising one or more probes that span the locus of, and are complementary to, one of the reference alleles;

step (a) comprises hybridizing the control sample and the target sample to each of the probe sets;

step (b) comprises measuring the intensity of first and second label to probes in each of the probe sets; and step (c) comprises determining a normalized intensity ratio of first label to second label for probes for each of the probe sets, wherein for each probe set the value of the ratio relative to one or more threshold values is an indicator of whether the target sample contains the reference allele complementary to the probes in the probe set, or the corresponding variant allele(s), or both reference and variant alleles.

16. The method of claim 15, further comprising preparing the target sample by multiplex amplification.

17. A method of analyzing a nucleic acid in a target sample, comprising:

(a) hybridizing a first-labelled control sample comprising one or more homozygous reference alleles, and a second-labelled target sample potentially comprising one or more variant alleles differing from one of the reference alleles at a locus within a region, to one or more probe sets, wherein (i) each probe set comprises probes attached to a substrate, probes within a probe set having overlapping sequences that are complementary to and span the region of one or more of the reference alleles, probes within a probe set being complementary to the same reference allele and probes in different probe sets being complementary to different reference alleles; and (ii) the first and second labels are different;

(b) measuring the intensity of first and second label bound to probes in the probe sets and determining a normalized intensity ratio of first label to second label for probes in the probe sets;

(c) identifying a subset of probes having a normalized intensity ratio that is altered relative to the normalized intensity ratio of the other probes within the same probe set, the identity of the probes within the subset of probes indicating the identity of a site of variation that potentially differs between one of the reference alleles and one of the variant alleles;

(d) hybridizing the control and test samples to a second substrate comprising a plurality of probe sets, each probe set complementary to a different possible variant allele at the potential site of variation;

(e) measuring the intensity of first and second label bound to each probe in the probe sets of the second substrate; and (f) determining from the measured intensities of step (e) which allele is present in the sample.

18. The method of claim 17, wherein the probe set is a plurality of probe sets.

19. The method of claim 18, wherein the probes in different probe sets are complementary to the reference form of a different gene.

20. The method of claim 17, further comprising washing the substrate with a wash solution to remove unbound alleles.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

ATTAACCCTC ACTAAAGGGA ATTAAATGAA AGAGTATGAG C      41

(2) INFORMATION FOR SEQ ID NO: 2:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 2:

TAATACGACT CACTATAGGG AGTGCTCCCA AAAGCATAAA                                           40

(2) INFORMATION FOR SEQ ID NO: 3:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 3:

CGGTAGCATC TTGAC                                                                     15

(2) INFORMATION FOR SEQ ID NO: 4:

(i) SEQUENCE CHARACTERISTICS:
          (A) LENGTH: 39 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 4:

GTTTCCCAGT CACACGGAAT TAAATGAAAG AGTATGAGC                                            39

(2) INFORMATION FOR SEQ ID NO: 5:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 5:

AGGAAACAGC TATGACCATG TGAGGGGACG CTCTTG                                               36

(2) INFORMATION FOR SEQ ID NO: 6:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 6:

GTTTCCCAGT CACACGTTGG GAAAACCTAT CGGAA                                                35

(2) INFORMATION FOR SEQ ID NO: 7:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 7:

AGGAAACAGC TATGACCATC TTTGGGGTCT TCAGCA                                               36

(2) INFORMATION FOR SEQ ID NO: 8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

GTTTCCCAGT CACACGTGTT CAAATACCAG TGAACTTA        38

(2) INFORMATION FOR SEQ ID NO: 9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

AGGAAACAGC TATGACCATG GAGCCCACTC ATTAGTAC        38

(2) INFORMATION FOR SEQ ID NO: 10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

GTTTCCCAGT CACACGCCAA GTACAGTGAG CACAATTA        38

(2) INFORMATION FOR SEQ ID NO: 11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

AGGAAACAGC TATGACCATG TGCTCCCAAA AGCATAAA        38